United States Patent
Suck et al.

(10) Patent No.: US 9,453,058 B2
(45) Date of Patent: *Sep. 27, 2016

(54) VARIANTS OF THE MAJOR ALLERGEN PHL P 1 FROM TIMOTHY GRASS

(75) Inventors: Roland Suck, Hamburg (DE); Helmut Fiebig, Schwarzenbek (DE); Oliver Cromwell, Schmilau (DE)

(73) Assignee: Merck Patent GmbH, Darmstadt (DE)

( * ) Notice: Subject to any disclaimer, the term of this patent is extended or adjusted under 35 U.S.C. 154(b) by 714 days.

This patent is subject to a terminal disclaimer.

(21) Appl. No.: 12/728,745

(22) Filed: Mar. 22, 2010

(65) Prior Publication Data

US 2012/0263741 A1  Oct. 18, 2012

Related U.S. Application Data (62) Division of application No. 10/525,000, filed as application No. PCT/EP03/08471 on Jul. 31, 2003, now Pat. No. 7,731,970.

(30) Foreign Application Priority Data

Aug. 19, 2002 (EP) .................................... 02018157

(51) Int. Cl.
| | | |
|---|---|---|
| A01N 37/18 | (2006.01) |
| A01N 63/00 | (2006.01) |
| A61K 38/00 | (2006.01) |
| A61K 39/00 | (2006.01) |
| A61K 39/35 | (2006.01) |
| A61K 39/36 | (2006.01) |
| A61K 48/00 | (2006.01) |
| C07H 21/02 | (2006.01) |
| C07H 21/04 | (2006.01) |
| C07K 2/00 | (2006.01) |
| C07K 4/00 | (2006.01) |
| C07K 5/00 | (2006.01) |
| C07K 14/415 | (2006.01) |

(52) U.S. Cl.
CPC .................................. C07K 14/415 (2013.01)

(58) Field of Classification Search
None
See application file for complete search history.

(56) References Cited

U.S. PATENT DOCUMENTS

| 7,001,743 | B2 | 2/2006 | Cosgrove | |
| 7,731,970 | B2 * | 6/2010 | Suck et al. ................. | 424/185.1 |
| 2002/0064530 | A1 | 5/2002 | Sturaro | |
| 2004/0034888 | A1 * | 2/2004 | Liu et al. ...................... | 800/289 |
| 2007/0011783 | A1 * | 1/2007 | Liu et al. ...................... | 800/289 |

FOREIGN PATENT DOCUMENTS

| EP | 0576426 B1 | | 1/1994 | |
| WO | WO 92/03550 | * | 3/1992 | ............ C12N 15/29 |
| WO | WO 0222679 | | 3/2002 | |

OTHER PUBLICATIONS

Focke et al. 'Nonanaphylactic synthetic peptides derived from B cell epitopes of the major grass pollen allergen, Phl p. 1, for allergy vaccination.' The FASEB Journal express article IO.1096/fj.OI-OO16fje. Published online Jul. 24, 2001. pp. 1-25.*

Kuby et al. 'Immunology.' Fourth Edition, Chapter 18: 449-465, 2000.*

Mukherjee et al. 'Allergic Asthma: Influence of Genetic and Environmental Factors.' The Journal of Biological Chemistry vol. 286(38):32883-32889, 2011.*

Suck et al., "Bacterially expressed and optimized recombinant phl p 1 is irnmunobiochemically equivalent to natural phl p 1.", Biochem Biophys. Acta. 1764 (11): 1701-9, 2006.

Focke et al., "Nonanaphylactic synthetic peptides derived from B cell epitopes of the major grass pollen allergen, Phi p 1, for allergy vaccination." 15 (11): 2042-4, Faseb J. Epub, Jul. 24, 2001.

Larche et at, "immunological mechanisms of allergen-specific immunotherapy,", Nature Reviews, (6): 761-771, 2006.

Schramm et al., "'Allergen engineering', variants of the timothy grass pollen allergen Phi p 5b with reduced IgE-binding capacity but conserved T cell reactivity.", J. Immunol., 162: 2406-2414, 1999.

Petersen et al. "Structural investigations of the major allergen Phl p 1 on the complementary DNA and protein level," J Allergy Clin Immunol., May 1995;95(5 Pt 1):987-94.

Laffer et al.,"Complementary DNA cloning of the major allergen Phl p I from timothy grass (Phleum pratense); recombinant Phl p I inhibits IgE binding to group I allergens from eight different grass species," J. Allergy Clin Immunol., 1994, 94: 689-698.

* cited by examiner

*Primary Examiner* — Nora Rooney
(74) *Attorney, Agent, or Firm* — Millen, White, Zelano, Branigan, P.C.

(57) ABSTRACT

The invention relates to pharmaceutically important variants of the major allergen Phl p 1 from timothy grass, characterized in that a preparation, hitherto not possible, of monomeric molecules which are soluble and stable in physiological media can be carried out with the aid of prokaryotic expression systems and subsequent purification thereof.

13 Claims, 3 Drawing Sheets

Figure 1:
SDS-PAGE of nPhl p 1, rPhl p 1-LM and rPhl p 1-HM

Figure 2: Gel filtration with rPhl p 1-HM and rPhl p 1-LM

..........rPhl p 1-HM       ———— rPhl p 1-LM

Elution at:      51.41 min           55.22 min

Figure 3:
EAST inhibition test with fold variants rPhl p 1-T236C-LM and -HM

VARIANTS OF THE MAJOR ALLERGEN PHL P 1 FROM TIMOTHY GRASS

This application is a divisional of U.S. patent application Ser. No. 10/525,000, filed Feb. 17, 2005, issued as U.S. Pat. No. 7,731,970, which is the US national phase under §371 of PCT/EP03/08471, filed Apr. 31, 2003, the disclosures of which are incorporated by reference herein in their entirety.

The invention relates to variants of the major allergen Phl p 1 from timothy grass, characterised in that a preparation, hitherto not possible, of monomeric molecules which are soluble and stable in physiological media can be carried out with the aid of prokaryotic expression systems and subsequent purification thereof.

BACKGROUND OF THE INVENTION

Type 1 allergies are of worldwide importance. Up to 25% of the population of industrialised countries suffer from complaints such as allergic rhinitis, conjunctivitis or bronchial asthma which are caused by allergens of various origin present in the air (aeroallergens), such as plant pollen, mites, cats or dogs. Up to 40% of these type 1 allergy sufferers in turn exhibit specific IgE (immunoglobulin E) reactivity in the case of grass pollen (Freidhoff et al., 1986, J. Allergy. Clin. Immunol. 78, 1190-201).

The substances which initiate type 1 allergy are proteins, glycoproteins or polypeptides. After uptake via the mucous membranes, these allergens react with the IgE molecules bonded to the surface of mast cells in sensitised people. If two IgE molecules are crosslinked to one another by an allergen, this results in the release of mediators (for example histamine, prostaglandins) and cytokines by the effector cell and thus in the corresponding clinical symptoms.

Depending on the relative frequency of the allergy sufferers having IgE antibodies against certain allergens, a distinction is made between major and minor allergens. In the case of timothy grass (*Phleum pratense*), Phl p 1 (Petersen et al., 1993, J. Allergy Clin. Immunol. 92, 789-796), Phl p 5 (Matthiesen and Löwenstein, 1991, Clin. Exp. Allergy 21, 297-307), Phl p 6 (Petersen et al., 1995, Int. Arch. Allergy Immunol. 108, 49-54) and Phl p 2/3 (Dolecek et al., 1993) have hitherto been characterised as major allergens and Phl p 4 (Löwenstein, 1978, Prog. Allergy 25, 1-62) and group 10 and 11 from *Lolium perenne* (Ansari et. al., 1987, J. Allergy Clin. Immunol. 80, 229-235) as minor allergens.

Group 1, which includes Phl p 1 from timothy grass, is classified as one of the most relevant allergen groups of grass pollen (Tamborini, E. et al., Eur. J. Biochem. 1997, 249:886-894). The other representatives of group 1 from other grasses have homologies of in some cases more than 95% to Phl p 1 (Petersen, A., et al., J. Allergy Clin. Immunol. 1995, 95: 987-994). Owing to the high homologies, reactions to the allergens of other cross-reactive species also occur in the case of sensitisation with a grass. For this reason, these molecules are of overriding importance for corresponding diagnostic and therapeutic approaches.

On therapeutic use of these allergens, use is made of the reaction with T helper cells, where reorientation of the pathological TH2 cells into the TH1 type occurs. This causes a change in the cytokine profile so that B cells are stimulated to form IgG instead of IgE.

A classical approach to effective therapeutic treatment of allergies is specific immunotherapy or hyposensitisation (Fiebig, 1995, Allergo J. 4 (6), 336-339, Bousquet et al., 1998, J. Allergy Olin Immunol. 102(4), 558-562), in which the patient is injected subcutaneously with natural allergen extracts in increasing doses.

However, there is a risk in this method of allergic reactions or even anaphylactic shock. In order to minimise these risks, innovative preparations in the form of allergoids are being employed. These are chemically modified allergen extracts which have significantly reduced IgE reactivity, but identical T-cell reactivity compared with the untreated extract (Fiebig, 1995, Allergo J. 4 (7), 377-382).

Even more substantial therapy optimisation would be possible with allergens prepared by recombinant methods. Defined cocktails, optionally matched to individual patients, of highly pure allergens prepared by recombinant methods could release extracts from natural allergen sources since these, in addition to the various allergens, contain a relatively large number of immunogenic, but non-allergenic accompanying proteins. Realistic perspectives which may result in reliable hyposensitisation with expression products are offered by specifically mutated recombinant allergens in which IgE epitopes are specifically deleted without impairing the T-cell epitopes which are essential for therapy (Schramm et al., 1999, J. Immunol. 162, 2406-2414).

A further possibility for therapeutic influencing of the disturbed Th-cell equilibrium in allergy sufferers is treatment with expressible DNA which encodes for the relevant allergens. Initial experimental evidence of allergen-specific influencing of the immune response has been furnished in rodents by ejection of allergen-encoding DNA (Hsu et al., 1996, Nature Medicine 2 (5), 540-544).

Phl p 1 is a protein comprising 240 amino acids and an n-glycosylation site. The glycosylation fraction is 5% of the molecular weight, which, in the natural protein, is about 30-35 kDa (Petersen et al., Allergy Clin. Immunol. 1995, 95: 987-994; Suck et al., J. Immunol. Meth. 1999, 229:73-80). The nucleic acid sequence of Phl p 1 is known (Laffer et al., J. Allergy Clin Immunol. 1994, 94: 689-698; Petersen et. al., J. Allergy Clin. Immunol., 1995, 95: 987-94) and can thus be utilised for the recombinant preparation of the molecule.

Previous attempts to prepare the molecule by recombinant methods in bacterial or eukaryotic systems, such as, for example, yeast, in such a way that a stable monomeric form was obtained were, however, unsuccessful owing to its poor solubility:

In the case of bacterial expression, Phl p 1 is deposited as inclusion bodies (Vrtala et al., J. Allergy. Clin. Immunol, 1996; 97: 781-7) and firstly has to be denatured before purification. The denaturing agent is subsequently removed. However, complete re-folding of the protein into the natural soluble conformation has hitherto not been achieved (Andersson, Lidholm, Int. Arch. Allergy Immunol. 2003; 130: 87-107).

One possible reason preventing the formation of a stable conformation could have been the absence of glycosylation. However, a stable Phl p 1 has not been obtained even in eukaryotic systems in which glycosylation is possible (K. Grobe, Dissertation, 1998, University of Hamburg).

Instead, a cause of the lack of solubility is assumed to be proteolytic activity, which results in self-degradation of the molecule (Grobe et al., Eur. J. Biochem. 1999; 263: 33-40; Kirsten Gehlhar, Dissertation, 1998, Medical University of Lübeck, Germany). In addition, hydrophobic interactions between the molecules are also possible as a cause of the aggregation.

The object on which the present invention is based thus consisted in the provision of variants of the major allergen Phl p 1 from timothy grass which are distinguished by improved solubility at the same time as full retention of the therapeutically and diagnostically important immunological properties and which can thus be purified in pharmaceutically suitable form.

FIGURES

Track 1: Molecular weight standard (10, 15, 20, 25, 30, 40, 50, 60, 70, 80, 90, 100, 120, 160, 220 kDa, bench mark protein ladder, Invitrogen, Karlsruhe, Germany)
Track 2: Extract from *Phleum pratense* pollen
Track 3: nPhl p 1
Track 4: rPhl p 1-LM
Track 5: rPhl p 1-HM

The figure shows that the two fold variants have different apparent molecular weights.

DETAILED DESCRIPTION OF THE INVENTION

Surprisingly, it has now been found that the introduction of an additional cysteine residue, preferably in the carboxyl-terminated part (in particular from amino acid position 140, very particularly preferably between amino acid positions 230 and 240) of the molecule, results in the improved solubility in accordance with the invention with unchanged IgE activity and T-cell reactivity.

The invention therefore relates to variants of the major allergen Phl p 1 from timothy grass which have an additional Cys residue compared with the wild type, and to fragments and variants derived from the base molecules which have the same or similar advantageous properties.

The invention furthermore relates to a process for the preparation of the variants according to the invention of the recombinant major allergen rPhl p 1, characterised in that, by methods known per se, a base triplet encoding for a Cys residue is introduced into the Phl p 1 gene by insertion or exchange, the gene modified in this way is overexpressed in a host organism, and the allergen variant obtained by overexpression is purified.

The prokaryotic recombinant preparation and purification can be carried out with or without a fusion component introduced by genetic engineering and always results in the same products. If a fusion component is used, it is preferably an His tag. The purification methods vary depending on the expression vector or system.

The present invention accordingly encompasses a specifically modified primary sequence of the recombinant allergen rPhl p 1 which facilitates the recombinant preparation thereof in bacterial or other expression systems and subsequent purification.

The invention thus also relates to DNA molecules which encode for the allergen variants according to the invention.

The recombinant proteins are autoproteolytically inactive and can therefore be stored in stable monomeric form in physiological, buffered or other solutions depending on the application. The T-cell stimulation exhibits no significant differences between recombinant and natural Phl p 1.

The recombinant allergen variants and the derived fragments or variants can thus be utilised for the therapy of grass pollen-induced allergic diseases.

Owing to this pharmaceutical suitability, the present invention also relates to the novel allergen variants in their property as medicaments.

The allergen variants and fragments prepared by recombinant methods can furthermore be utilised for the diagnosis of pollen allergies.

In the preparation of the major allergen Phl p 1 from timothy grass modified by genetic engineering, the amino acid exchange is effected by targeted nucleotide exchange, for example by means of PCR. In a particularly preferred embodiment, the mutant rPhl p 1-A236C in accordance with SEQ ID NO 2, the alanine at position 236 is replaced by cysteine. However, the exchange site can also be at any desired other site of the molecule. In general, however, it will be localised in the C-terminal region of the molecule, preferably from position 140, in particular between positions 230 and 240.

As a consequence of the exchange, the proteolytic activity known for Phl p 1 is simultaneously eliminated.

As a further unexpected effect, two fold variants which can be completely separated from one another occur during the isolation and purification of the molecule in accordance with the invention.

Figure 1:
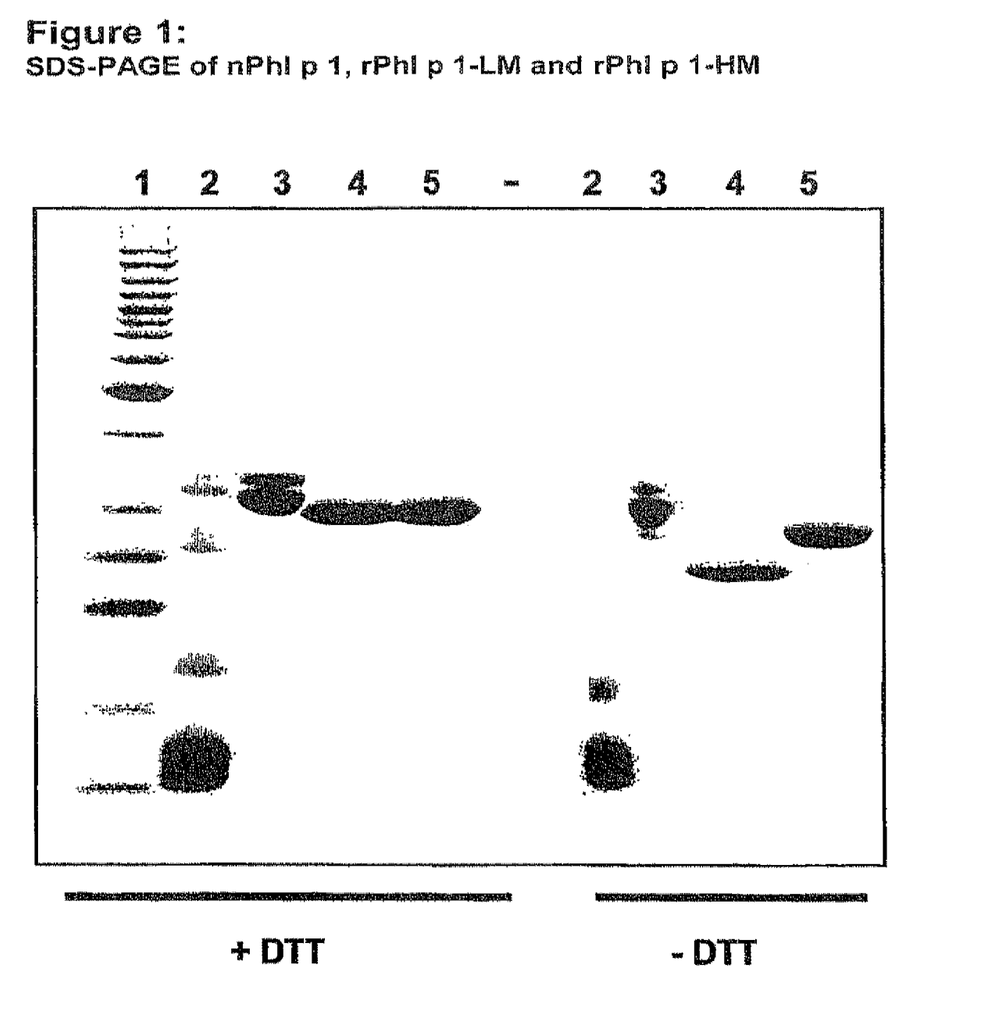
FIG. 1: SDS-PAGE of wild type nPhl p 1 (n=natural) and fold variants LM and HM of allergen variant rPhl p 1-A236C (r=recombinant) under reducing conditions (in the presence of dithiothreitol DTT) and non-reducing conditions (without DTT).
Figure 2:
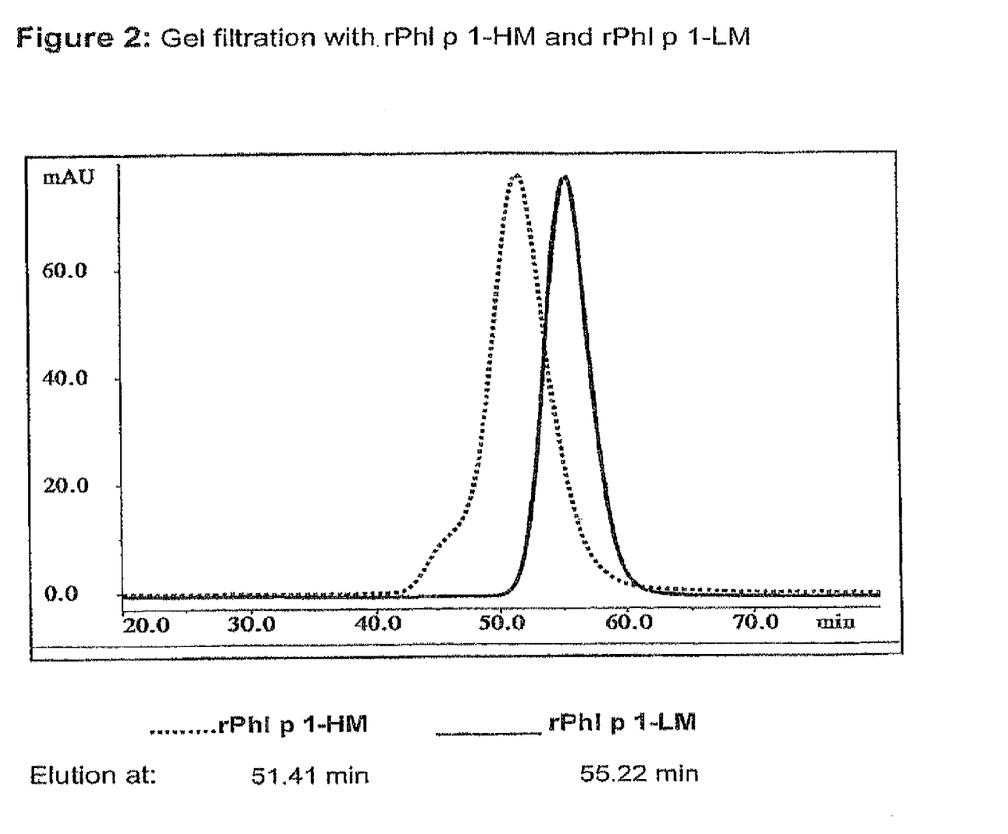
FIG. 2: Gel filtration with rPhl p 1-HM and rPhl p 1-LM on a Sephacryl S100 column.

While the first conformation variant, referred to as rPhl p 1-LM (LM=low molecular weight), exhibits very similar behaviour to the natural protein owing to its similar or identical run behaviour in the non-reduced SDS-PAGE (FIG. 1) and gel filtration (for example on Sepharcryl S-100, cf. FIG. 2), the second variant, referred to as rPhl p 1-HM (HM=high molecular weight), exists in a different fold form. The IgE reactivity also differs. While rPhl p 1-LM has a reactivity comparable to the natural protein, rPhl p 1-HM is bound less well by IgE antibodies and is particularly suitable for specific immunotherapy owing to its hypoallergeneity (see FIG. 3).

In principle, however, both fold forms are suitable both for therapeutic and for diagnostic applications.

The invention thus furthermore relates to different fold forms of the rPhl p 1 allergen variant according to the invention and to the use thereof for therapeutic and diagnostic purposes.

Both fold forms are readily soluble, stable in monomeric form and have no detectable proteolytic/autoproteolytic activity.

The allergen variants according to the invention can be obtained, for example, by the two preparation processes outlined below—with or without artificial fusion component:

1) Expression with Artificial Fusion Component (His tag)

In the case of the use of an His tag, the purification of the initially insoluble crude protein is carried out via a plurality of biochemical separation steps, comprising one or more metal ion chelate affinity chromatography steps and removal of the His tag. For pre- and post-purification, various other chromatography methods and de- and renaturing steps can be used.

Preparation of fold form rPhl p 1-LM:
  denaturing of the inclusion bodies isolated from the host organism using guanidinium chloride,
  renaturing of the dissolved protein on a chelate affinity chromatography column,
  removal of the His tag,
  first gel filtration,
  chelate affinity chromatography,
  isolation of the target protein from the flow-through,
  second, final gel filtration.

The other fold form—rPhl p 1-HM—can be obtained in this purification variant by carrying out the following process steps:
  denaturing of the inclusion bodies isolated from the host organism using guanidinium chloride,
  renaturing of the dissolved protein on a chelate affinity chromatography column,
  removal of the His tag,
  first gel filtration,
  chelate affinity chromatography,
  elution of the target protein with an imidazole gradient,
  second, final gel filtration.

2) Expression without fusion component (without His tag)
  Denaturing of the inclusion bodies isolated from the host organism using guanidinium chloride, where, as described below, one or other fold form is obtained depending on the denaturing duration.
  Renaturing of the dissolved protein by dilution in buffer solution, where 20-50 mM Tris/HCl pH 7-8 is preferably used, but other buffers and pH values (for example 7-10.5) are also possible. For dilution, the denaturing batch is preferably added to a multiple of its volume (about 10 to 80 times, preferably 20 to 60 times the volume) of the preferably stirred or otherwise mixed buffer solution—for example by decantation, pipetting or pumping; however, the buffer solution can also be added to the denaturing batch. The rate of addition is not crucial: thus, the entire amount can be added in one portion within a few seconds or alternatively—(but preferably not necessarily) uniformly—distributed over a number of hours.
  Concentration and purification of the renatured protein by chelate affinity chromatography and subsequent elution with an imidazole gradient (use is preferably made of a step gradient, but a continuous gradient is likewise possible). Alternatively or additionally to the chelate affinity chromatography, hydrophobic interaction chromatography and/or an anion exchange chromatography can optionally also be carried out (the molecules must be treated completely by chromatography).
  Final gel filtration.

The alternative stable fold forms LM and HM can be obtained specifically here with minimal cross-contamination by means of different incubation times in the denaturing step. For the preparation of the LM form, incubation can basically be carried out for between about 1 and 50 hours. In general, however, a range from 10 to 40 hours, preferably from 15 to 30 hours, will be used, where a range from 18 to 22 hours is particularly preferred.

For the HM variant, significantly longer incubation times are required. They are in the order of from 60 to 120 hours. However, incubation will usually be carried out for from 70 to 100 hours, particularly preferably in a range of from 80 to 90 hours.

The denaturing step is in all cases followed by the above-described dilution step with buffer solution.

The interval between (about 50 to 60 hours) represents the re-formation phase. The dilution step apparently fixes the folding process, no further kinetics take place.

The fine purification for the separation of LM and HM is possible via hydrophobic interaction chromatography or is achieved by gel filtration, in which the forms have significantly different retention times.

The allergen variants according to the invention can be obtained in high purity in their fold variants LM and HM and have valuable pharmaceutically relevant properties. Thus, they can be employed as a mixture, but also individually, for diagnosis (in particular rPhl p 1-LM owing to the retention of IgE activity) and therapy (in particular rPhl p 1-HM owing to the reduced IgE activity) of allergic diseases.

The invention therefore likewise relates to the use of the allergen variants and/or pharmaceutically usable derivatives thereof, including mixtures thereof in all ratios, for the preparation of a medicament for specific immunotherapy (hyposensitisation) and diagnosis of allergies in the triggering of which the major allergen Phl p 1 from timothy grass is involved.

The invention furthermore relates to a pharmaceutical composition comprising an allergen variant according to the invention and/or pharmaceutically usable derivatives thereof, including mixtures thereof in all ratios, and, if desired, excipients and/or adjuvants. The active ingredients according to the invention can be converted into a suitable dosage form here together with at least one solid, liquid and/or semi-liquid excipient or adjuvant and, if desired, in combination with one or more further active ingredients.

If the DNA molecules on which the allergen variants according to the invention are based are ligated to a suitable expression vector, these constructs can in addition be used as preparations for immunotherapy (DNA vaccination).

The invention therefore likewise relates to a recombinant DNA expression vector containing a DNA molecule according to the invention for the treatment of allergies in the triggering of which the major allergen Phl p 1 from timothy grass is involved, by immunotherapeutic DNA vaccination.

The invention furthermore relates to the use of the said expression vector and/or derivatives thereof, including mixtures thereof in all ratios, for the preparation of a medicament for the treatment of allergies in the triggering of which the major allergen Phl p 1 from timothy grass is involved, by immunotherapeutic DNA vaccination.

Finally, the invention relates to a pharmaceutical composition comprising the said expression vector and/or pharmaceutically usable derivatives thereof, including mixtures thereof in all ratios, and, if desired, excipients and/or adjuvants, for the treatment of allergies in the triggering of which the major allergen Phl p 1 from timothy grass is involved, by immunotherapeutic DNA vaccination.

For the purposes of this invention, pharmaceutical compositions can be used as therapeutic agents in human or veterinary medicine. Suitable excipients are organic or inorganic substances which are suitable for parenteral administration and do not react with allergen variants according to the invention of the major allergen Phl p 1 from timothy grass. Suitable for parenteral administration are, in particular, solutions, preferably oil-based or aqueous solutions, furthermore suspensions, emulsions or implants. The allergen variants according to the invention may also be lyophilised and the resultant lyophilisates used, for example, for the preparation of injection preparations. The compositions indicated may be sterilised and/or comprise adjuvants, such as lubricants, preservatives, stabilisers and/or wetting agents, emulsifiers, salts for modifying the osmotic pressure, buffer substances and/or a plurality of further active ingredients.

Furthermore, delayed-release compositions can be obtained by corresponding formulation of the allergen variants according to the invention, for example by adsorption on aluminium hydroxide.

Further selective modifications at different positions and other modifications—for example for increasing the hypoallergeneity—are of course also possible via the mutations according to the invention. These modifications can be, for example, chemical modifications of the allergen extract (Fiebig, 1995, Allergo J. 4 (7), 377-382). However, they can also be carried out at the DNA level by genetic engineering, where, for example, amino acid insertions, deletions and exchanges, cleavage of the protein into fragments and fusion of the protein or fragments thereof to other proteins or peptides are suitable.

In view of the high sequence homologies within group 1 grass pollen major allergens, all the effects described here for Phl p 1 relating to the improvement in the solubility by the introduction of a Cys residue and the occurrence of fold variants can also be expected for other representatives of this group.

Even without further comments, it is assumed that a person skilled in the art will be able to utilise the above description in its broadest scope. The embodiments depicted below in Tables 1 and 2 by way of example for the variant rPhl p 1-A236C should therefore merely be regarded as descriptive disclosure which is absolutely not limiting in any way.

All chromatography materials are commercially available from Amersham Biosciences (Freiburg, Germany).

The choice of metal ion in the chelate affinity chromatography methods described is not crucial, both Ni and Cu can be used.

Example 1

Isolation of rPhl p 1-A236C-LM and -HM

Purification Variant with His Tag

The sequence encoding for Phl p 1 was amplified by means of PCR with 5'- and 3'-specific oligonucleotides and ligated into a pProEx vector (GIBCO, La Jolla, USA) via the Ehe I and Hind III restriction site. The 3'-primer was modified from GC to TG at base position 706/707 in such a way that an alanine-encoding triplet is converted into a cysteine-encoding triplet (Essential Molecular Biology; T. A. Brown ed., IRL Press, Oxford, 1994). The transformation was carried out in *E. coli* origami. The starting vector pProEx selected supplies the 6xHis sequence localised at the N-terminal end, followed by a recognition sequence for the TEV protease. The recombinant, primarily 6xHIS-tagged rPhl p 1-A236C molecules present as insoluble aggregates after bacterial expression are dissolved after pre-purification in 6 M guanidinium chloride (GdmCl), 50 mM Tris/HCl, 500 mM NaCl, pH 8.0). This is followed by two-stage Ni chelate affinity chromatography:

In a first step, the proteins bonded to chelating Sepharose under denaturing conditions are transferred by a gradient over the course of 90 min from the denaturing solution into a buffer consisting of 50 mM phosphate buffer and 500 mM NaCl (pH 7.4). This is followed by stepwise elution with 500 mM imidazole in phosphate buffer. The renatured fusion protein is cleaved into rPhl p 1 and the 6xHis fusion component by means of a specific TEV protease.

For preparation for a second affinity chromatography, a gel filtration is carried out with Sephadex G-25 and phosphate buffer as eluent, as a result of which the imidazole is removed.

The rebuffered protein mixture is then employed for a second Ni chelate affinity chromatography. In this, some of the successfully cleaved rPhl p 1 is found in the flow-through. This is the LM form of the molecule. Besides uncleaved molecules, the conformation variant HM also remains adhering to the column, apparently due to exposed histidine residues. This cleaved variant elutes before the uncleaved fusion proteins in an imidazole gradient, enabling this form also to be obtained in high purity. In a final step, a gel filtration with Superdex 75 is carried out for final purification and transfer into a desired solvent.

TABLE 1

Overview of the preparation and purification process according to the invention using an His tag 1. Expression
2. Isolation of the inclusion bodies
3. Denaturing
4. Ni chelate affinity chromatography 1 (renaturing)
5. Removal of the His tag
6. Gel filtration (Sephadex G-25)
7. Ni chelate affinity chromatography 2: Flow-through: rPhl p 1-LM
   Eluate: rPhl p 1-HM,
   Uncleaved His-rPhl p 1 fusion protein
8. Gel filtration (Superdex 75)

Example 2

Isolation of rPhl p 1-A236C-LM and -HM

Purification Variant without His Tag

Initially, the procedure in accordance with Example 1 is followed, but where the vector selected does not supply a fusion protein as primary product.

The recombinant, primarily rPhl p 1-A236C molecules present as insoluble aggregates (inclusion bodies) after bacterial expression, are dissolved after pre-purification in 6M guanidinium chloride (GdmCl), 50 mM Tris/HCl, pH 8.0). This is followed by 40-fold dilution in 20 mM Tris pH 8.0. To this end, the denaturing solution is decanted into the dilution solution stirred using a magnetic stirrer.

a) Preparation of the LM Form

The inclusion bodies are incubated in the denaturing solution for 20 h and subsequently diluted as described above.

b) Preparation of the HM Form

The inclusion bodies are incubated in the denaturing solution for 85 h and subsequently diluted as described above.

500 mM NaCl are added to the respective dilution (renaturing) batch. The dissolved molecules in the renaturing batch are concentrated via Cu chelate affinity chromatography and eluted with 200 mM imidazole in phosphate buffer as stage (or gradually through 500 mM imidazole in phosphate buffer).

The chelate affinity chromatography can optionally be utilised for conditioning before elution of the protein by, for example, using a 3 M NaCl solution for washing and a 3 M NaCl, 200 mM imidazole solution for the elution. The eluate, which has a high salt content, could then be employed directly for hydrophobic interaction chromatography.

In a final step, a gel filtration with Superdex 75 is carried out for final purification and transfer into a desired solvent.

TABLE 2

Overview of the preparation and purification process according to the invention without use of an His tag 1. Expression
2. Isolation of the inclusion bodies
3. Denaturing  Duration 20 h: LM
   Duration 85 h: HM
4. Dilution
5. Cu chelate affinity chromatography
6. Gel filtration (Superdex 75)

Example 2

Figure 3:
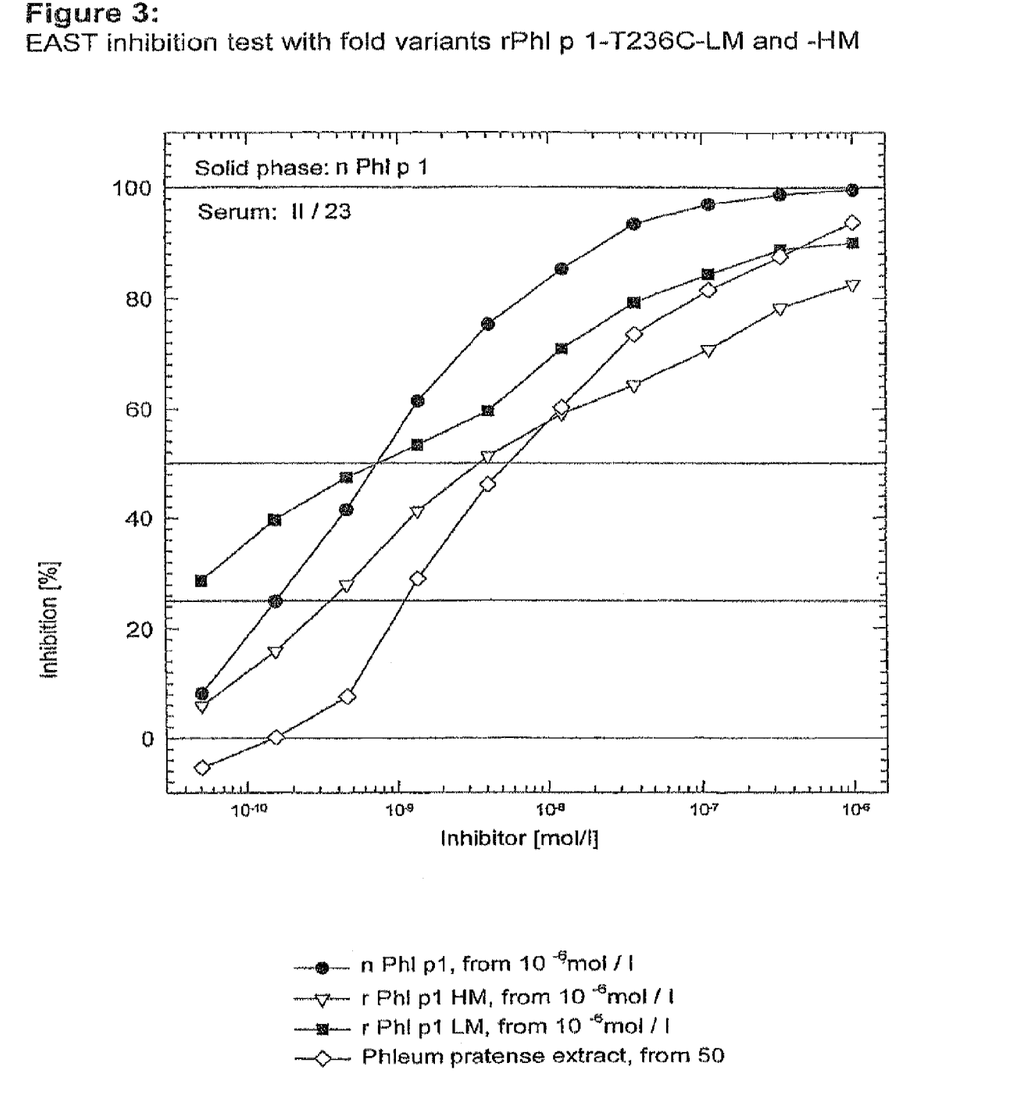
FIG. 3: Enzyme allergo-sorbent test (EAST) for quantification of the IgE bonding of fold variants rPhl p 1-A236C-LM and -HM The concentration of an inhibitor of IgE-nPhl p 1 bonding in mol/l is plotted on the horizontal axis, the degree of inhibition in [%] is indicated on the vertical axis. The measurement was carried out with nPhl p 1 on the solid phase and a typical serum of a grass pollen allergy sufferer.

Different IgE Bonds of the Wild Type and of Fold Variants LM and HM of Allergen Variant rPhl p 1-A236C Natural nPhl p 1 and recombinant rPhl p 1 variants HM and LM are compared with one another with respect to the strength of their IgE bonding in an EAST inhibition assay carried out by the method of Suck et al. (Int. Arch. Allergy Immunol. 2000; 121: 284-291) with an allergy sufferer serum pool (FIG. 3). It is found that the HM variant is significantly reduced in its IgE bonding compared with natural Phl p 1 protein, while the LM variant has IgE bonding which is comparable to natural Phl p 1 protein.

The invention claimed is:

1. A polypeptide variant of a wild type major allergen Phl p 1 from timothy grass, consisting essentially of
    (a) the amino acid sequence of SEQ ID NO:2, which consists of the wild type major allergen Phl p 1 having a single cysteine (Cys) amino acid substitution A236C, or
    (b) the amino acid sequence of SEQ ID NO:2, but having the wild type A236 amino acid and a single Cys amino acid substitution at any other amino acid from amino acid position 140 to 240 of SEQ ID NO:2,
and optionally further consisting of a histidine (His) tag for purification purposes.

2. The polypeptide variant of claim 1, which is
    (i) the polypeptide encoded by the polynucleotide of SEQ ID NO: 1; or
    (ii) the polypeptide of SEQ ID NO: 2.

3. The polypeptide variant of claim 1, which is a recombinant polypeptide variant (rvPhl p 1).

4. The polypeptide variant of claim 1, which exists in multiple fold forms.

5. A pharmaceutical composition comprising the polypeptide variant of claim 1 and a pharmaceutically acceptable carrier.

6. A fold form of rvPhl p 1-LM of the recombinant polypeptide variant of claim 3, which is obtainable by:
    overexpressing in a non-human host organism, a recombinant fusion polypeptide consisting of the polypeptide variant and a His tag;
    denaturing inclusion bodies isolated from the host organism using guanidinium chloride;
    renaturing fusion polypeptide on a chelate affinity chromatography column eluted with imidizole;
    cleaving the His tag;
    removing the imidazole by gel filtration;
    purifying the polypeptide variant free of His tag from the recombinant fusion polypeptide variant using chelate affinity chromatography;
    isolating the polypeptide variant fold form LM free of His tag from the flow-through; and
    purifying the polypeptide variant fold form LM free of His tag lay gel filtration.

7. The fold form rvPhl p 1-HM of the recombinant polypeptide variant of claim 3, which is obtainable by:
    overexpressing in a non-human host organism, a recombinant fusion polypeptide consisting of the polypeptide variant and a His tag;
    denaturing inclusion bodies isolated from the host organism using guanidinium chloride;
    renaturing fusion polypeptide on a chelate affinity chromatography column eluted with imidizole;
    cleaving the His tag;
    removing the imidazole by gel filtration;
    purifying the polypeptide variant free of His tag from the recombinant fusion polypeptide variant using chelate affinity chromatography;
    eluting the polypeptide variant fold form HM free of His tag with an imidazole gradient; and
    purifying the polypeptide variant free of His tag by gel filtration.

8. A process for the preparation of the polypeptide variant of claim 1, comprising
    (1) expressing a polynucleotide which encodes the polypeptide variant in a non-human host organism to obtain a polypeptide variant product, and
    (2) purifying the polypeptide variant product.

9. The process of claim 8, wherein the purification (2) comprises
    denaturing an insoluble crude polypeptide variant product obtained in (1), renaturing the insoluble polypeptide variant product by dilution, and biochemically purifying the renatured polypeptide variant product to obtain a soluble form of the recombinant polypeptide variant.

10. The process of claim 8, wherein the polypeptide variant is expressed as the polypeptide variant having the His tag for purification purposes, and the purification (2) comprises
    employing a plurality of biochemical purification steps comprising a two-stage metal ion chelate affinity chromatography, and removing the His tag.

11. A process for the preparation of the polypeptide variant of claim 1, comprising culturing a non-human host cell which comprises a vector encoding the polypeptide variant under conditions sufficient to express the polypeptide variant; and purifying the polypeptide variant from the culture.

12. A method for specific immunotherapy of an allergy triggered by major allergen Phl p 1 from timothy grass, comprising administering to a subject in need thereof an effective amount of the polypeptide variant of claim 1 or a pharmaceutical composition comprising the polypeptide variant.

13. A method for the diagnosis of an allergy which is triggered by major allergen Phl p 1 from timothy grass, comprising administering to a subject in need thereof a diagnostically effective amount of the polypeptide variant of claim 1 or a pharmaceutical composition comprising the polypeptide variant.

* * * * *

SEQUENCE LISTING

<160> NUMBER OF SEQ ID NOS: 2

<210> SEQ ID NO 1
<211> LENGTH: 723
<212> TYPE: DNA
<213> ORGANISM: Phleum pratense
<220> FEATURE:
<221> NAME/KEY: CDS
<222> LOCATION: (1)..(720)
<223> OTHER INFORMATION:

<400> SEQUENCE: 1

```
atc ccc aag gtt ccc ccc ggc ccg aac atc acg gcg acc tac ggc ggc      48
Ile Pro Lys Val Pro Pro Gly Pro Asn Ile Thr Ala Thr Tyr Gly Gly
1               5                   10                  15 aag tgg ctg gac gcg aag agc acc tgg tac ggc aag ccg acg gcc gcc      96
Lys Trp Leu Asp Ala Lys Ser Thr Trp Tyr Gly Lys Pro Thr Ala Ala
            20                  25                  30 ggt ccc aag gac aac ggc ggc gcg tgc ggg tac aag gac gtg gac aag     144
Gly Pro Lys Asp Asn Gly Gly Ala Cys Gly Tyr Lys Asp Val Asp Lys
        35                  40                  45 ccc ccg ttc agc ggc atg acc ggc tgc ggc aac acc ccc atc ttc aag     192
Pro Pro Phe Ser Gly Met Thr Gly Cys Gly Asn Thr Pro Ile Phe Lys
    50                  55                  60 tcc ggc cgg ggc tgc ggc tcc tgc ttc gag atc aag tgc acc aag ccc     240
Ser Gly Arg Gly Cys Gly Ser Cys Phe Glu Ile Lys Cys Thr Lys Pro
65                  70                  75                  80 gag gcc tgc tcc ggc gag ccc gtg gtg gtc cac atc acc gac gac aac     288
Glu Ala Cys Ser Gly Glu Pro Val Val Val His Ile Thr Asp Asp Asn
                85                  90                  95 gag gag ccc atc gcc gcg tac cac ttc gac ctc tcc ggc atc gcg ttc     336
Glu Glu Pro Ile Ala Ala Tyr His Phe Asp Leu Ser Gly Ile Ala Phe
            100                 105                 110 ggg tcc atg gcc aag aag ggc gac gag cag aag ctg cgc agc gcc ggc     384
Gly Ser Met Ala Lys Lys Gly Asp Glu Gln Lys Leu Arg Ser Ala Gly
        115                 120                 125 gag gtg gag atc cag ttc cgc cgc gtc aag tgc aag tac ccg gag ggc     432
Glu Val Glu Ile Gln Phe Arg Arg Val Lys Cys Lys Tyr Pro Glu Gly
    130                 135                 140 acc aag gtg acc ttc cac gtg gag aag ggg tcc aac ccc aac tac ctg     480
Thr Lys Val Thr Phe His Val Glu Lys Gly Ser Asn Pro Asn Tyr Leu
145                 150                 155                 160 gcg ctg ctg gtg aag ttt gtc gcc ggc gac ggc gac gtg gtg gcg gtg     528
Ala Leu Leu Val Lys Phe Val Ala Gly Asp Gly Asp Val Val Ala Val
                165                 170                 175 gac atc aag gag aag ggc aag gac aag tgg atc gcg ctc aag gag tcg     576
```

```
Asp Ile Lys Glu Lys Gly Lys Asp Lys Trp Ile Ala Leu Lys Glu Ser
            180                 185                 190 tgg gga gcc atc tgg agg atc gac acc ccg gag gtg ctc aag ggc ccc      624
Trp Gly Ala Ile Trp Arg Ile Asp Thr Pro Glu Val Leu Lys Gly Pro
            195                 200                 205 ttc acc gtc cgc tac acc acc gag ggc ggc acc aag ggc gag gcc aag      672
Phe Thr Val Arg Tyr Thr Thr Glu Gly Gly Thr Lys Gly Glu Ala Lys
            210                 215                 220 gac gtc atc ccc gag ggc tgg aag gcc gac acc tgc tac gag tcc aag      720
Asp Val Ile Pro Glu Gly Trp Lys Ala Asp Thr Cys Tyr Glu Ser Lys
225                 230                 235                 240 tga                                                                   723

<210> SEQ ID NO 2
<211> LENGTH: 240
<212> TYPE: PRT
<213> ORGANISM: Phleum pratense

<400> SEQUENCE: 2

Ile Pro Lys Val Pro Gly Pro Asn Ile Thr Ala Thr Tyr Gly Gly
1                5                  10                  15

Lys Trp Leu Asp Ala Lys Ser Thr Trp Tyr Gly Lys Pro Thr Ala Ala
            20                  25                  30

Gly Pro Lys Asp Asn Gly Gly Ala Cys Gly Tyr Lys Asp Val Asp Lys
            35                  40                  45

Pro Pro Phe Ser Gly Met Thr Gly Cys Gly Asn Thr Pro Ile Phe Lys
50                  55                  60

Ser Gly Arg Gly Cys Gly Ser Cys Phe Glu Ile Lys Cys Thr Lys Pro
65                  70                  75                  80

Glu Ala Cys Ser Gly Glu Pro Val Val His Ile Thr Asp Asp Asn
            85                  90                  95

Glu Glu Pro Ile Ala Ala Tyr His Phe Asp Leu Ser Gly Ile Ala Phe
            100                 105                 110

Gly Ser Met Ala Lys Lys Gly Asp Glu Gln Lys Leu Arg Ser Ala Gly
            115                 120                 125

Glu Val Glu Ile Gln Phe Arg Arg Val Lys Cys Lys Tyr Pro Glu Gly
            130                 135                 140

Thr Lys Val Thr Phe His Val Glu Lys Gly Ser Asn Pro Asn Tyr Leu
145                 150                 155                 160

Ala Leu Leu Val Lys Phe Val Ala Gly Asp Gly Asp Val Val Ala Val
            165                 170                 175

Asp Ile Lys Glu Lys Gly Lys Asp Lys Trp Ile Ala Leu Lys Glu Ser
            180                 185                 190

Trp Gly Ala Ile Trp Arg Ile Asp Thr Pro Glu Val Leu Lys Gly Pro
            195                 200                 205

Phe Thr Val Arg Tyr Thr Thr Glu Gly Gly Thr Lys Gly Glu Ala Lys
            210                 215                 220

Asp Val Ile Pro Glu Gly Trp Lys Ala Asp Thr Cys Tyr Glu Ser Lys
225                 230                 235                 240
```